United States Patent [19]

Moyne et al.

[11] Patent Number: 4,883,612

[45] Date of Patent: Nov. 28, 1989

[54] PREPARATION OF PARA-ACYLOXYBENZENE SULFONATES

[75] Inventors: José Moyne, Caluire; Camille Disdier, Lyons, both of France

[73] Assignee: Rhone-Poulenc Chimie de Base, Courbevoie, France

[21] Appl. No.: 51,226

[22] Filed: May 14, 1987

Related U.S. Application Data

[63] Continuation of Ser. No. 702,732, Feb. 19, 1985, abandoned.

[30] Foreign Application Priority Data

Feb. 17, 1984 [FR] France ................... 84 02399

[51] Int. Cl.$^4$ ............... C07C 143/46; C07C 143/38
[52] U.S. Cl. .................................. 260/402; 560/142
[58] Field of Search .............. 560/142; 260/410.5, 260/402

[56] References Cited

U.S. PATENT DOCUMENTS

| | | | |
|---|---|---|---|
| 2,694,720 | 11/1954 | Denton et al. | 560/142 |
| 2,805,248 | 9/1957 | Friederich et al. | 560/232 |
| 3,600,431 | 8/1971 | Taylor et al. | 260/410.5 |
| 4,285,971 | 8/1981 | Muntwyler | 260/410.5 |
| 4,496,584 | 1/1985 | Fujii et al. | 260/410.5 |
| 4,587,054 | 5/1986 | Hardy et al. | 260/410.5 |
| 4,588,532 | 5/1986 | Moyne et al. | 560/142 |

OTHER PUBLICATIONS

Kirk-Othmer *Encyclopedia of Chemical Technology* 2nd Ed. vol. 8 (1965) p. 335.

*Primary Examiner*—Donald B. Moyer
*Assistant Examiner*—Patricia M. Scott
*Attorney, Agent, or Firm*—Burns, Doane, Swecker & Mathis

[57] ABSTRACT p-Acyloxybenzene sulfonates, well suited for detergency applications, are facilely and rapidly prepared by acylating an alkali or alkaline earth metal, or ammonium p-phenol sulfonate, with an anhydride of a straight or branched chain carboxylic acid having from 7 to 12 carbon atoms, in a polar aprotic solvent and in the presence of a catalytically effective amount of an alkali or alkaline earth metal salt of a straight or branched chain aliphatic carboxylic acid having from 7 to 12 carbon atoms.

19 Claims, No Drawings

PREPARATION OF PARA-ACYLOXYBENZENE SULFONATES

This application is a continuation of application Ser. No. 702,732, filed Feb. 19, 1985, now abandoned.

CROSS-REFERENCE TO RELATED APPLICATION

Our copending application, Ser. No. 702,733, U.S. Pat. No. 4,588,532, filed concurrently herewith and assigned to the assignee hereof.

BACKGROUND OF THE INVENTION

1. Field of the Invention

The present invention relates to the preparation of para-acyloxybenzene sulfonates, and, more especially, to the preparation of para-acyloxybenzene sulfonates by basic catalysis, and wherein the acyloxy moiety of such sulfonates contains from 7 to 12 carbon atoms.

2. Description of the Prior Art

It is known to this art, from French Pat. No. 2,164,619, Example 1, to prepare the title compounds from an aliphatic acid chloride and potassium phenol sulfonate by direct condensation in an anhydrous reaction medium. The speed of condensation between the acid chloride and the phenol sulfonate is extremely slow (20 hours at 150° C.) and the product formed is very difficult to isolate. A large amount of HCl also forms in the process and is not always easy to eliminate.

It is also known [see Pueschel, Tenside, 7 (5), pp. 249–54 (1970)] to prepare these compounds by a method which differs slightly from that of French Pat. No. 2,164,619, but in the presence of an acid acceptor to avoid the elimination of gaseous hydrochloric acid. The product formed is neutralized by sodium carbonate, but as a result it is very difficult to separate the product obtained from the sodium chloride formed during neutralization.

The slowness of the reaction in which the acid chloride is condensed with the phenol sulfonate has prompted those skilled in this art to raise the reaction temperature considerably, but strongly colored products are then formed. Since such products are in fact principally used in detergency, however, it is necessary to produce perfectly white materials in order to meet commercial requirements.

It too is known, from French Pat. No. 2,299,321, to prepare para-acyloxybenzene sulfonates by condensing a powdered phenol sulfonate with acetic anhydride in vapor state; the reaction can be carried out dry, for acetic anhydride has a boiling point of 140° C., but it is not possible to proceed in this fashion as a means for condensing, e.g., nonanoic anhydride, with phenol sulfonate, since nonanoic anhydride has a boiling point of 260° C.

Nonetheless, it was hitherto unknown to condense an acid anhydride with a phenol sulfonate in a liquid reaction medium.

SUMMARY OF THE INVENTION

Accordingly, a major object of the present invention is the provision of an improved process for the preparation of para-acyloxybenzene sulfonates which is both quick and easy, is carried out in a liquid reaction medium, gives rise to the production of an easily separated reaction product in completely colorless state, and which otherwise avoids those disadvantages and drawbacks to date characterizing the state of this art.

Briefly, the present invention features the preparation of para-acyloxybenzene sulfonates having the general formula (I):

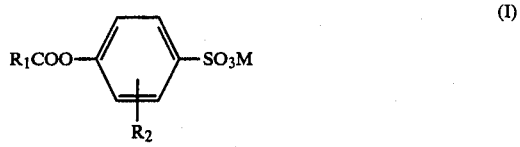

wherein $R_1$ is a straight or branched chain aliphatic radical containing from 6 to 11 carbon atoms, $R_2$ is hydrogen, halogen, an alkyl radical having from 1 to 4 carbon atoms or the radical $-SO_3M$, and M is an alkali or alkaline earth metal or an ammonium group, by acylating an alkali or alkaline earth metal or ammonium phenol sulfonate with an anhydride of a straight or branched chain carboxylic acid containing from 7 to 12 carbon atoms, in a polar aprotic solvent and in the presence of a catalytically effective amount of an alkali or alkaline earth metal salt of a straight or branched chain aliphatic carboxylic acid having from 7 to 12 carbon atoms.

DETAILED DESCRIPTION OF THE INVENTION

More particularly according to the present invention, exemplary reactant aliphatic anhydrides include heptanoic, octanoic, caprylic, nonanoic, pelargonic, decanoic, capric, dodecanoic, and lauric anhydrides. Preferably employed are the anhydrides of those carboxylic acids containing 9 carbon atoms. More preferred are pelargonic anhydride and 3,5,5-trimethylhexanoic anhydride, since these materials are readily commercially available.

The reactant acid anhydrides may be prepared in known manner by any one of a number of processes. In a first embodiment, described in Collective Organic Syntheses, 3, p. 28, John Wiley (1955), the acid chloride is contacted with the acid and a tertiary base, which will neutralize the acid formed. This gives the required anhydride and a hydrochloride with a tertiary base. In a second embodiment, described in Journal of Chemical Society, p. 755 (1964), the acid chloride and the sodium salt of the acid are contacted in water. This gives the required anhydride and sodium chloride. Since the reaction is carried out in water, the anhydride formed need not be easily hydrolyzable.

In a third embodiment, acetic anhydride is reacted with the acid according to the following mechanism:

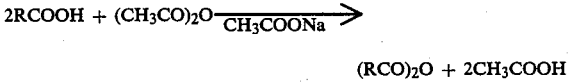

It is preferred to carry out this particular reaction in the presence of an excess of acetic anhydride, which is distilled upon completion of the reaction.

Consistent herewith, it is preferred to use an acid anhydride which has been obtained in accordance with the aforesaid third embodiment.

As regards the various phenol sulfonates, it is preferred to use those in which $R_2$ is hydrogen, and more preferably the phenol sulfonate of sodium or potassium, since these compounds are the most readily commercially available.

Representative of the polar aprotic solvents intended, the following are exemplary:
(i) dimethylformamide;
(ii) N-methylpyrrolidone;
(iii) dimethylacetamide;
(iv) dimethylsulfoxide; and
(v) sulfolane The solvent should nevertheless be odorless, for it is commercially impossible to incorporate a malodorous substance in a detergent. The boiling point of the solvent must not be too high, and its manufacturing cost must be low enough not to impose an unnecessary increase in the cost of the product to be obtained. From among all of the solvents intended, dimethylformamide is the preferred as it best conforms to the aforesaid conditions.

The alkali or alkaline earth metal salt of a carboxylic acid having from 7 to 12 carbon atoms, and which is used as the catalyst for the condensation reaction, has the following general formula (II):

$$R_3COOM \qquad (II)$$

wherein M is an alkali or alkaline earth metal, and $R_3$ is a straight or branched chain alkyl radical having from 6 to 11 carbon atoms. It is preferred to use the sodium salt of the same acid as that used to form the anhydride, since this avoids incorporating any chemical reagent foreign to those of the reaction.

To obtain a proper reaction speed it is preferable to use a molar excess of the anhydride relative to the phenol sulfonate. For a proper economic yield it is still more preferable to add an excess of anhydride of at least 0.2 mole and preferably from 0.2 to 0.3 mole relative to the stoichiometry of the reaction.

The molar ratio of solvent to phenol sulfonate preferably ranges from 5 to 50. A larger amount is not outside of the scope of the invention, but such amounts will have to be adapted to the economics of the process. The molar ratio more preferably ranges from 5 to 10 and still more preferably from 7 to 10.

The molar ratio of the compound (II) to the phenol sulfonate preferably is in excess of about 0.005 and more preferably ranges from 0.01 to 0.02.

The reaction temperature influences the speed of reaction; accordingly, a temperature in excess of 80° C. is advantageous. However, higher temperatures are not deleterious to the process of the invention. All that is necessary is to adapt the temperature to the economics of the process. The preferred reaction temperature thus ranges from 90° to 100° C.

The reaction is typically carried out at atmospheric pressure, although a higher pressure is also not deleterious to the process of the invention.

The final products according to the invention may facilely be extracted from the reaction medium by salting them out with acetone, at a temperature of 90° C. or above, and preferably from 90° to 100° C., by adding approximately the same weight of acetone as that of solvent introduced.

The title para-acyloxybenzene sulfonates are used in detergency applications, notably as surfactants. Especially representative formula (I) compounds are: sodium p-3,5,5-trimethylhexanoyloxybenzene sulfonate, sodium p-octanoylbenzene sulfonate and sodium p-dodecanoyloxybenzene sulfonate.

In order to further illustrate the present invention and the advantages thereof, the following specific examples are given, it being understood that same are intended only as illustrative and in nowise limitative.

EXAMPLE 1

Preparation of the sodium p-3,5,5-trimethylhexanoyloxybenzene sulfonate:

[1] Preparation of 3,5,5-trimethylhexanoic anhydride (TMH anhydride):

A 1000 liter reactor was used, having a distillation column at the top thereof. It was charged with 583 kg of trimethylhexanoic acid (3.69 Kmoles), 282 kg of acetic anhydride (2.76 Kmoles) and 0.1 kg of sodium acetate. The catalyst was selected because it only slightly discolored the TMH anhydride. The reaction medium was brought to 90° C. at a vacuum of 12,000 Pa to allow for distillation of the acetic acid formed; the vacuum was then adjusted as the temperature of the distillation vessel rose. The reaction was complete after 3 hours, at:
T° = 110° C.;
Pressure = 6,660 Pa The reaction mixture was adjusted to 160° C. (at 1,300 Pa) to eliminate the excess acetic anhydride.

The very slightly colored 3,5,5-trimethylhexanoic anhydride was not distilled but was used as such:
Weight = 550 kg;
Yield = 100%

[2] Condensation of TMH anhydride with sodium p-phenol sulfonate:

A 3 m³ reactor was used, with a small column ascending thereabove. 794 kg (10.9 Kmoles) of dimethylformamide, 301 kg (1.53 Kmoles) of sodium p-phenol sulfonate dried at 160° C. and 2,600 Pa ($H_2O < 0.5\%$) and 3 kg (0.016 Kmole) of sodium isononanoate were charged into the reactor.

The reaction medium was brought to 90° C. and 550 kg (1.84 Kmoles) of TMH anhydride (20% excess) were introduced over one half to three quarters of an hour.

The temperature was maintained for three hours.

794 kg of acetone were added at 90° to 100° C. to salt out the ester which was in solution in the DMF.

The material was cooled to room temperature.

The ester was filtered, under pressure, through a filter having a surface area of 6 m².

The filtered product was washed in acetone and dried at 150° C. and 2,600 Pa.
Weight = 500 kg;
Yield = 96%

The solutions were distilled and recycled.

EXAMPLE 2

Preparation of sodium p-2-ethylhexanoyloxybenzene sulfonate:

[1] Preparation of 2-ethylhexanoic anhydride:

The 2-ethyl hexanoic anhydride was prepared under the same conditions as in the previous example.

[2] Condensation of 2-ethylhexanoic anhydride with sodium p-phenol sulfonate:

66 g (0.9 mole) of DMF, 25 g (0.127 mole) of dehydrated sodium para-phenol sulfonate and 0.35 g (0.002 mole) of sodium 2-ethylhexanoate were charged into a 250 cm³ reactor.

The reaction medium was brought to 100° C. and 45 g (0.160 mole), i.e., 25% excess of 2-ethylhexanoic anhydride, were added over 45 minutes.

The reaction was continued for 2 hours, 30 min, at that temperature.

80 g of acetone were then added at a temperature of 100° C.

The reaction product was cooled to room temperature and then filtered.

The ester was washed with acetone and dried at 150° C. and 2600 Pa, to give:

Weight = 39 g sodium p-2-ethylhexanoylbenzene sulfonate

Yield = 95%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a paraacyloxybenzene sulfonate having the general formula (I):

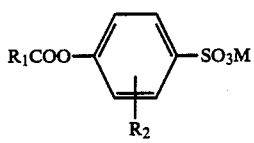

wherein $R_1$ is a straight or branched chain aliphatic radical having from 6 to 11 carbon atoms, $R_2$ is hydrogen, halogen, an alkyl radical having from 1 to 4 carbon atoms, or the radical —$SO_3M$, and M is an alkali or alkaline earth metal, or ammonium, which process comprises acylating an alkali or alkaline earth metal, or ammonium p-phenol sulfonate, with an anhydride of a straight or branched chain carboxylic acid having from 7 to 12 carbon atoms, in a polar aprotic solvent and in the presence of a catalytically effective amount of an alkali or alkaline earth metal salt of a straight or branched chain aliphatic carboxylic acid having from 7 to 12 carbon atoms, the molar ratio of polar aprotic solvent to p-phenol sulfonate ranging from 5 to 50.

2. The process as defined by claim 1, said p-phenol sulfonate comprising sodium or potassium p-phenol sulfonate.

3. The process as defined by claim 1, said acid anhydride comprising an anhydride of a carboxylic acid having 9 carbon atoms.

4. The process as defined by claim 1, said polar aprotic solvent comprising dimethylformamide, dimethylacetamide, N-methyl pyrrolidone, dimethylsulfoxide or sulfolane.

5. The process as defined by claim 4, said polar aprotic solvent comprising dimethylformamide.

6. The process as defined by claim 1, said catalytic salt comprising the sodium salt of the same carboxylic acid as that which comprises the anhydride.

7. The process as defined by claim 1, wherein the molar ratio of acid anhydride to p-phenol sulfonate is at least 1.2.

8. The process as defined by claim 1, wherein the molar ratio of solvent to p-phenol sulfonate ranges from 5 to 10.

9. The process as defined by claim 8, wherein the molar ratio of solvent to p-phenol sulfonate ranges from 7 to 10.

10. The process as defined by claim 1, wherein the molar ratio of catalytic salt to p-phenol sulfonate is in excess of about 0.005.

11. The process as defined by claim 10, wherein the molar ratio of catalytic salt to p-phenol sulfonate ranges from 0.01 to 0.02.

12. The process as defined by claim 1, wherein the reaction temperature is in excess of about 80° C.

13. The process as defined by claim 1, further comprising salting the product para-acyloxybenzene sulfonate out of the mixture of reaction with acetone.

14. The process as defined by claim 13, said salting out being at a temperature of at least 90° C.

15. The process as defined by claim 13, said salting out being with an amount of acetone approximately the same as the amount of solvent present.

16. The process as defined by claim 7, said molar ratio ranging from 1.2 to 1.3.

17. The process as defined by claim 12, said reaction temperature ranging from 90 to 100° C.

18. The process as defind by claim 1, said acid anhydride comprising heptanoic, octanoic, nonanoic, decanoic, or dodecanoic lauric anhydride.

19. The process as defined by claim 1, said acid anhydride comprising pelargonic anhydride or 3,5,5-trimethylhexanoic anhydride.

* * * * *